United States Patent [19]

Reiser

[11] Patent Number: 5,064,291
[45] Date of Patent: Nov. 12, 1991

[54] METHOD AND APPARATUS FOR INSPECTION OF SOLDER JOINTS UTILIZING SHAPE DETERMINATION FROM SHADING

[75] Inventor: Kurt Reiser, Hawthorne, Calif.
[73] Assignee: Hughes Aircraft Company, Los Angeles, Calif.
[21] Appl. No.: 504,460
[22] Filed: Apr. 3, 1990
[51] Int. Cl.$^5$ .................. G01B 11/00; H04N 7/00
[52] U.S. Cl. ................................ 356/372; 356/376; 356/394; 358/101; 358/106
[58] Field of Search ............... 356/372, 375, 376, 394, 356/237; 250/561, 571; 358/101, 106, 107

[56] References Cited
U.S. PATENT DOCUMENTS

| 4,650,333 | 3/1987 | Crabb et al. | 356/376 |
| 4,677,302 | 6/1987 | Chiu et al. | 356/376 |
| 4,677,473 | 6/1987 | Okamoto et al. | 356/376 |
| 4,929,845 | 5/1990 | Amir et al. | 356/394 |

Primary Examiner—Richard A. Rosenberger
Assistant Examiner—Hoa Pham
Attorney, Agent, or Firm—V. D. Duraiswamy; W. K. Denson-Low

[57] ABSTRACT

Inspection of solder joints utilizing ilumination, reflected light intensity measurements to determine surface heights and comparison with predetermined inspection criteria to determine the integrity of the solder joint. A solder fillet (16b) is sequentially illuminated from first and second angles and optically scanned and reflected light intensity values at incremental values of inclination are measured. The heights of the fillet wall (16d) at predetermined points and the integrity of the fillet (16b) are determined using the measured reflected light intensity values and either using real-time computation or accessing an array of predetermined incremental inclination values as a function of the reflected light intensity values. Alternatively, the ratio of the sensed reflected light intensity values at each point may be used as an input variable to a one dimensional look-up table or for real-time computation. The solder fillet may be coated with a matte coating.

32 Claims, 5 Drawing Sheets

METHOD AND APPARATUS FOR INSPECTION OF SOLDER JOINTS UTILIZING SHAPE DETERMINATION FROM SHADING

BACKGROUND OF THE INVENTION

1. Field of the Invention

The present invention generally relates to the art of automated inspection of electrical components, and more particularly to a method and apparatus for optical inspection of solder joints which determines the shape of the joint from the shading or reflected light intensity of its surface.

2. Description of the Related Art

Commercial mass production of electrical circuitry relies heavily on automated soldering of components to circuit boards. Although manufacturing technology has advanced to the point where as many as 97% of mechanically soldered joints may be defect free, quality control requires that the solder joints be inspected in an attempt to reject defectively soldered assemblies before they are shipped to end users. Government specifications require that solder joints be inspected visually, and detail the visual appearance of good and bad solder joints.

Solder joint inspection has conventionally been performed by human inspectors viewing the joints through microscopes. However, there may be great variation among the decisions made by different inspectors, and even the performance of a single inspector can vary markedly over time. This is understandable since the inspectors may be required to view as many as three thousand solder joints in a single thirty minute period.

Several systems have been proposed for replacing human inspectors with automated solder joint inspection apparatus, including the use of X-ray imaging and computerized processing of the X-ray image. An exemplary system of this type is manufactured by the IRT Corporation of San Diego, Calif., and designated as model no. CXI-5210. The apparatus passes X-rays from a collimated, narrow-beam source through a solder joint on a circuit board to form a visible light image on a fluorescent screen. A video camera produces a digitized or pixelized image of the visible image on the screen, which is input into a computer for making inspection decisions for each image based on software programmed with the quality standards for the particular circuit board. Although X-ray systems are capable of providing detailed inspection results, they are incompatible with visual inspection standards.

Another system which utilizes an infrared detector to sense the thermal signature of a solder joint subjected to extreme temperature changes is presented in a paper entitled "Combining Soldering with Inspection", by R. Vanzetti et al, IEEE Control Systems Magazine, Oct. 1988, pp. 29–32. The main disadvantage of this system when applied to actual practice is a low level of reliability in distinguishing good solder joints from bad joints, and does not measure visual criteria.

Systems based on visible light and machine vision detection have also been developed. One such system is described in a paper entitled "A Three-Dimensional Approach to Automated Solder Joint Inspection", by S. Chen, in Electronic Manufacturing, Nov. 1988. The system is based on structured light, or light of a known shape or structure. It is projected onto an object, and the reflection of the light is viewed by a camera located at a fixed angle from the projector. The distortion of the reflected light from the known projected shape is used to compute the distance of every point on the object from the projector and camera. The reconstructed three dimensional shape is processed by software programmed with predetermined inspection criteria.

Another three dimensional optical system is described in an article entitled "A Tiered-Color Illumination Approach for Machine Inspection of Solder Joints", by D. Capson et al, IEEE Transactions on Pattern Analysis and Machine Intelligence, vol. 10, no. 3, May 1988, pp. 387–393. In this system, a tiered lighting arrangement is used to generate color contours on the solder joint for the detection and classification of defects. Each type of defect gives rise to a characteristic pattern of color contours which are processed using binary image techniques on each color plane of the image. Geometric descriptors measuring the shape of the color contours and the color level intensities of the solder joint images are used to identify each defect class. The resolution of the system, however, is very coarse, and may be insufficient to provide reliable solder joint inspection in many applications.

Another three dimensional optical system is manufactured by Robotic Vision Systems, Inc., (RVSI) of Hauppauge, N.Y., under the product designation HR-2000. The apparatus uses an optical triangulation three dimensional vision method to make thousands of measurements on every solder joint. The resulting data set forms a high resolution geometric map of the solder joint and the surrounding board and component. All data are directly measured, and no data have to be inferred to make critical decisions.

The main disadvantage of three dimensional optical image processing systems is that large and expensive computers and specialized hardware including moving parts are required to obtain acceptable speed and throughput.

SUMMARY OF THE INVENTION

The basic principle of the present "shape from shading" technique is that the shading of a surface, and thereby the intensity of light reflected from the surface, vary as the orientation of the surface changes relative to the viewer and light source. If the manner in which a surface reflects light, position of the viewer, and position of the light source are known, information about the orientation of the surface, more specifically the inclination or tilt thereof, can be derived. The present method and apparatus utilize reflected light intensity measurements to obtain the height profile of a solder joint fillet, or a side of a solder joint, and compare the profile with a predetermined criterion to determine the integrity of the fillet.

The present invention is especially advantageous for the inspection of solder joints. However, the principle of the invention may also be applied to determine the height of a surface of any object which has a substantially constant albedo or reflectance coefficient, and whose reflectance properties are known.

In accordance with the present invention, a solder surface is illuminated from a first angle, and tilted through a range of inclination. The values of reflected light intensity at incremental values of inclination are measured. The procedure is repeated from a second illumination angle. An array of incremental inclination values as a function of the measured reflected light intensity values at the two illumination angles is obtained. An incremental scan step is multiplied by the tangents of the inclination angles to obtain a corresponding array of incremental solder surface height changes. A solder fillet is sequentially illuminated from the first and second angles and optically scanned along lines extending from a base thereof to predetermined points on the fillet wall. The array is accessed using intensity values obtained at incremental points along the scan to obtain incremental height change values as a function of sensed first and second reflected light intensity values obtained from illumination of the fillet from the first and second angles respectively, which are summed to obtain heights of the fillet wall at the predetermined points. The heights are compared with a predetermined inspection criterion to determine the integrity of the fillet. A matte coating may be utilized to give the coated solder a lower, more uniform value of albedo or reflectance.

The reflected light intensity values in the array are determined empirically. However, an interpolation algorithm may be applied to fill in values where measurements are not taken over the entire range of surface inclination. Determination of surface tilt using illumination from two angles produces a unique, or unambiguous value. However, the invention may be practiced using only one illumination source. This alternative enables a simplified configuration, and may be advantageously employed in applications in which ambiguity resulting from equivalent values of reflected light intensity at two angles of inclination is not a problem. The invention may be embodied using one optical scanner and two light sources, in which case the solder joint is scanned once with only the first light source turned on, and again with only the second light source turned on. An equivalent result may be produced using two scanners and one light source, enabling the two scans to be performed simultaneously. Where the scanner is capable of recording several multicolor images simultaneously, for example three primary color images which may be combined to produce a full color image, the light sources may produce light of two different colors, and the scanner may produce separate images corresponding to the two colors respectively. This enables the invention to be practiced with one multi-color camera and two light sources, with the two images being obtained simultaneously.

The tilt may alternatively be computed in real time by solving an equation which approximates the relationship between reflected light intensity and tilt using the sensed values of reflected light intensity as input variables. A further alternative method of practicing the invention includes computing the ratio of the two sensed reflected light intensities at each point, and using the ratio as an input to a one-dimensional look-up table or for real-time computation using an equation.

These and other features and advantages of the present invention will be apparent to those skilled in the art from the following detailed description, taken together with the accompanying drawings, in which like reference numerals refer to like parts.

DETAILED DESCRIPTION OF THE INVENTION

Figure 1:
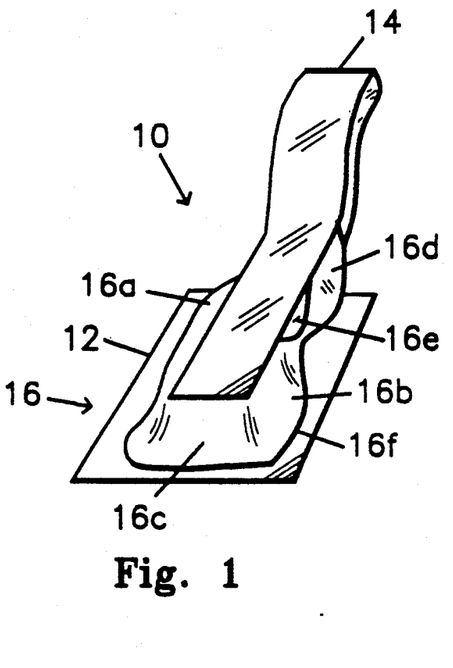
FIG. 1 is a perspective view of a solder joint to which the present invention is applicable.

Referring now to FIG. 1 of the drawing, a solder joint is generally designated as 10, and includes a metallic pad 12 provided on the surface of a circuit board or the like (not shown). A metallic lead 14 extending from an electrical component such as a flat-pack integrated circuit chip (not shown) extends downwardly into contact with the pad 12. The lead 14 is electrically connected to the pad 12 by means of a mass of solder 16 which defines fillets 16a, 16b, and 16c on the left and right sides and lower end of the lead 14 respectively. Considering the right fillet 16b for purposes of description, it will be seen that it has a generally concave wall 16d.

Solder joints are subject to a number of defects which the present invention may be used to detect, including bridging, misalignment, misshapen joint (dewet, unsoldered, insufficiently soldered), etc. A particular type of defect will be considered in describing the principles of the invention as illustrated in FIG. 1. As shown, the height of the fillet 16b is lower in an intermediate area 16e than in the remainder of the fillet 16b, exposing part of the right side of the lead 14. Generally, a solder joint is considered defective if more than one half of the side of a lead is exposed. Thus, if the height profile of the solder joint can be determined along a line on the fillet in contact with the lead, it can be compared with a predetermined criterion using an appropriate algorithm to compute the proportion of the lead that is exposed. These operations are performed automatically by the present invention, enabling a large number of solder joints to be tested or inspected for defects with a high degree of reliability at high speed.

The basic principle of the present "shape from shading" technique is that the apparent brightness or shading of a surface varies as the orientation of the surface changes relative to the viewer and illumination source. The brightness is proportional to the albedo or reflectance coefficient of the surface, and also proportional to the intensity and direction of the illumination source. For the purposes of the invention, it will be assumed that the apparent brightness is a function of the reflectance of the surface and varies only in accordance with the orientation, since the other factors have fixed values for a given light source configuration and may be lumped together as a single proportionality constant. In accordance with the present invention, if the albedo of the reflecting surface and characteristics of the illumination source are known, the inclination or tilt of the surface can be determined as a function of the reflected light intensity of the surface.

The first step in developing the shape from shading system for solder joints is to model the way solder reflects light. One result of the soldering process is a whitish substance which appears irregularly all over the fillets. Solder covered with this residual has dramatically different reflectance properties than naked solder. The shape from shading system relies on the assumption that the albedo of the fillet is constant over the entire surface thereof. Rather than just lying on top of the solder, the white residual seems intimate with the surface of the solder, resisting attempts to remove it with friction and/or solvents. It has been determined empirically that the shape from shading system works better with duller surfaces, or surfaces with lower values of albedo, and therefore works better with solder fillets which are evenly coated with the white residual than with no residual whatsoever. One solution to this problem is to apply a coating to the solder joints, masking the uncovered solder and creating uniform albedo over the surface of the fillet. A commercial spray product made by the Krylon company as product designation "Matte Finish no. 1311" has been determined to produce satisfactory results in coating the solder joints such that the solder surface has substantially constant albedo, while reducing the albedo of the solder surface to a value lower than that of naked solder.

Figures 2, 5:
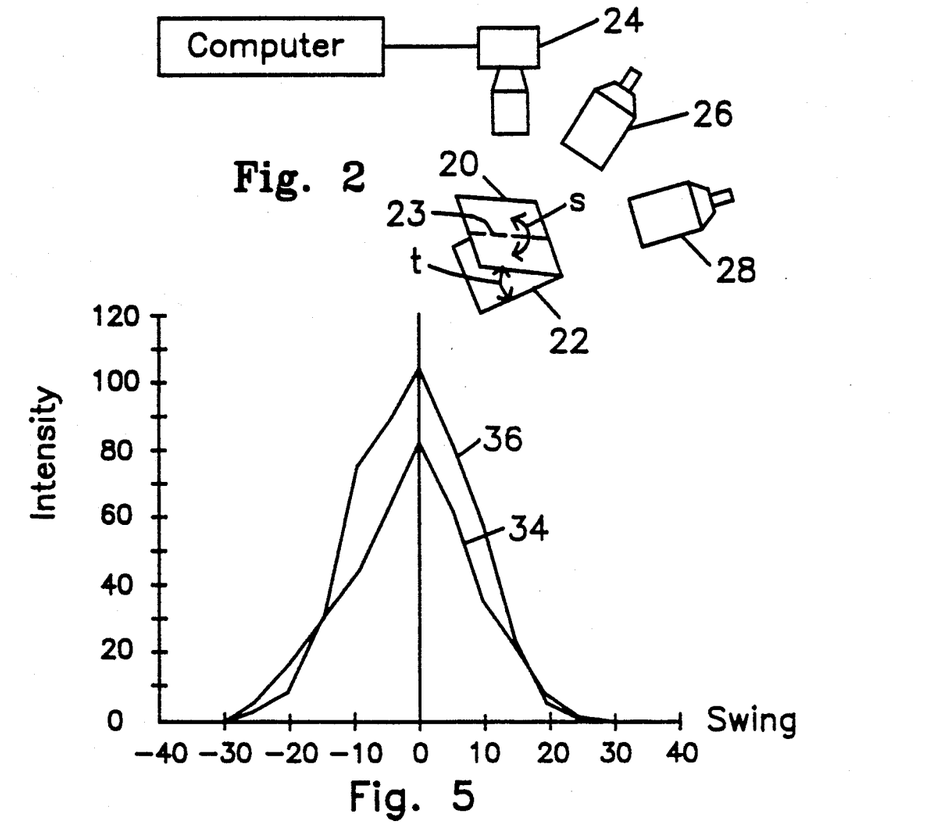
FIG. 2 is a simplified perspective view of an apparatus utilized to obtain reflected light intensity measurements for application in the invention.
FIGS. 5 and 6 are graphs further illustrating the principles of the invention.

The reflectance properties of solder were modelled using the arrangement illustrated in FIG. 2. A flat metal plate 20 was coated with solder, and the upper surface thereof was covered with a coating of the Krylon product referenced above to provide a coated solder surface having uniform or constant albedo. The plate 20 was mounted on a ramp 22 which was configured such that the angle of tilt or inclination t of the plate 20 could be varied from 0° to 90° from the vertical. A scanner 24 including a charge coupled device (CCD) camera, and first and second directional light sources 26 and 28 respectively embodied by fiber optics were mounted in the plane of tilt of the plate 20. The axes of the light sources 26 and 28 were tilted at angles of 35° and 70° from the vertical respectively. These angles are not, however, limitative of the scope of the invention and may be varied over a considerable range. It is also possible to obtain equivalent results using a single light source, and sequentially mounting it at the positions of the light sources 26 and 28.

Figure 3:
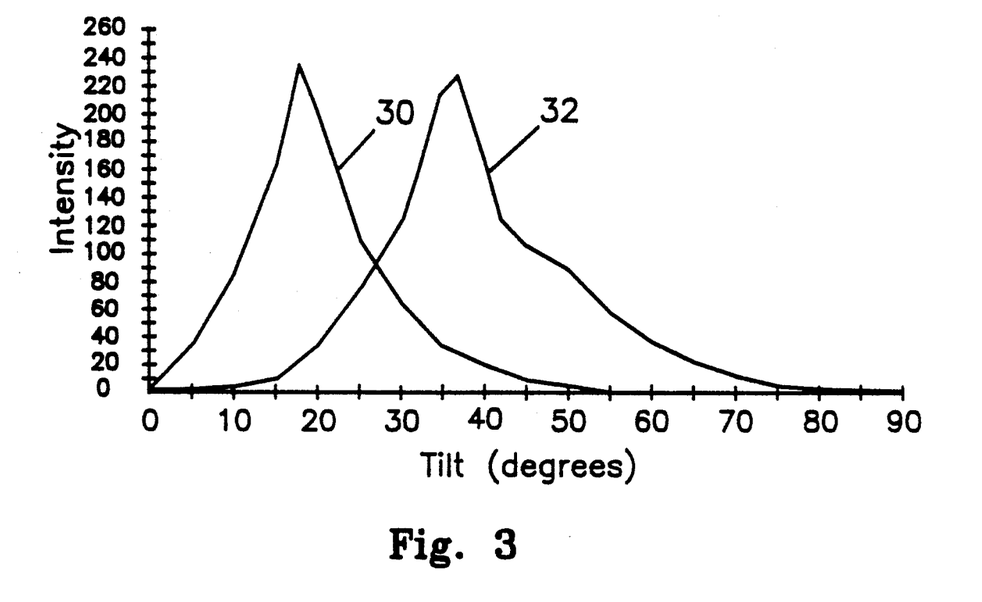
FIG. 3 is a graph illustrating the principles of the invention.

The light source 26 was first turned on with the light source 28 turned off, the plate 20 tilted through a range of inclination from 0° to 90°, and the reflected light intensity or shading I of the surface of the plate 20 sensed at incremental values of inclination to produce a curve 30 shown in FIG. 3. Then, the light source 28 was turned on with the light source 26 turned off, and the procedure repeated to produce a curve 32 shown in FIG. 3. The numerical values of reflected light intensity I represent the output of a CCD camera which stores a digitized or pixelized image, with each pixel having a maximum numerical value of 255 (8 bits or binary digits).

Application of the coating produces curves such as shown in FIG. 3, which are sufficiently spread out to obtain a range of reflected light intensity values suitable for practicing the invention. Pure, uncoated solder produces curves which appear as almost straight, vertical lines, with a very small angular range between maximum and minimum values.

The left curve in FIG. 3 indicates that when illuminated with a light tilted 35° off the vertical, all pixels with intensity 100 correspond to a surface tilt of either 11° or 26°. This is an illustration of the fact that images taken under a single light source direction are ambiguous with respect to surface orientation. Given a pixel with some intensity, one never knows which of two possible orientations is correct. The ambiguity can be alleviated by taking a second image of the same scene, this time using a light source at a different orientation. Continuing the previous example, the right curve in FIG. 3 shows that when the light is tilted at 70°, pixels oriented at 11° will have intensities near 0 whereas pixels at 26° will have intensities near 80. Thus, the second light source can be used to discern the correct orientation of pixels ambiguous under the first light source. The key points of this example are that images taken under a single light source direction are ambiguous with respect to surface orientation, and that additional images taken with different lighting directions can be used to unambiguously recover surface tilt.

Although determination of tilt using only one illumination source is theoretically ambiguous, if the known solder surface inclination is predetermined to vary within a range which excludes one of the values, the invention may be practiced using only one light source. As will be proven mathematically below, unambiguous tilt or inclination determination can be obtained using two light sources. This is illustrated in FIG. 3, such that for each value of tilt, there is a unique combination of intensity values from each of the curves 30 and 32 respectively.

Figure 4:
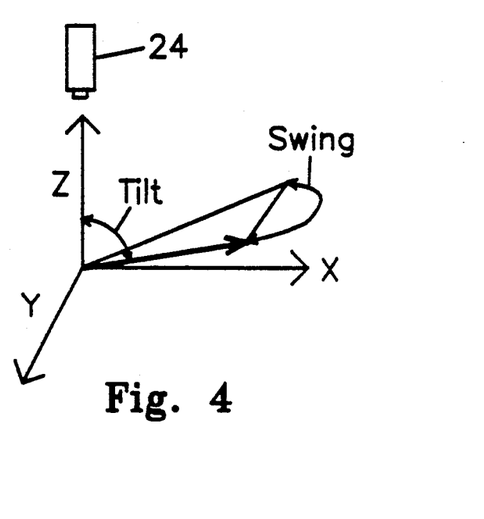
FIG. 4 is a diagram of the axial system illustrating variation of tilt and swing values in the apparatus of FIG. 2.

The graphs of FIG. 3 were obtained by varying a single orientation parameter, tilt or inclination. As illustrated in FIG. 4, it is further possible to vary the orientation of the plate 20 by varying the swing thereof, or the rotation of the plate 20 about a line 23 defined by the intersection of the plate 20 with the plane in which the scanner 24 and light sources 26 and 28 are mounted. Graphs 34 and 36 illustrated in FIG. 5 were obtained by fixing the tilt at values of 25° and 40° respectively, and varying the swing. The two curves are similar, with one almost appearing to be a multiple of each other.

Figure 6:
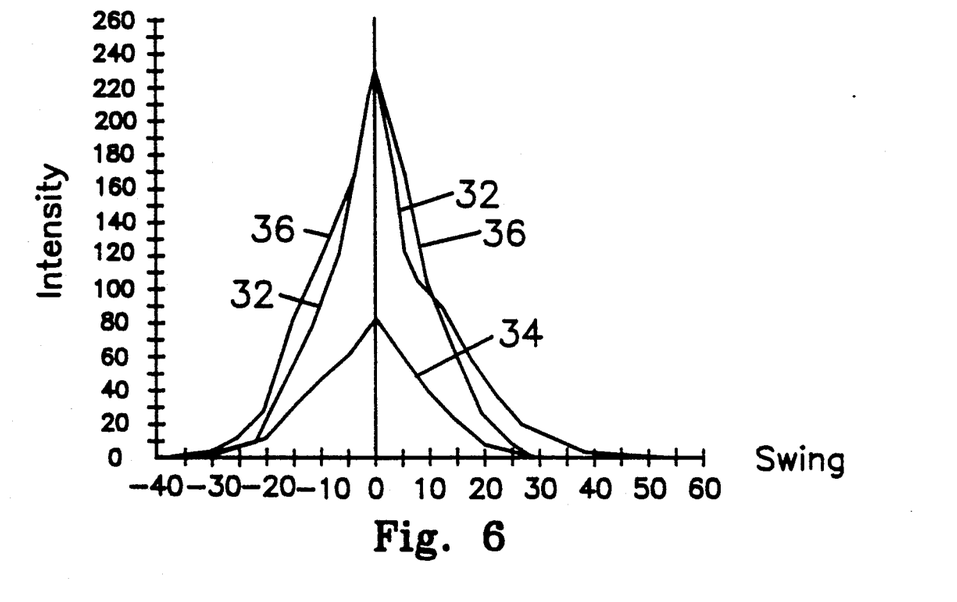

In FIG. 6, the curve 32 from FIG. 3 obtained by varying tilt with swing held constant, and the curve 34 obtained by varying swing with tilt held constant, are plotted about the same point on the horizontal axis. In addition, the curve 34 is scaled up to have the same vertical extent as the curve 32, and illustrated as a third curve 36. It will be noted that the experimentally obtained curves 32 and 36 are almost identical. This suggests that a single function of one variable is operating in both cases, being scaled and shifted in the different contexts. The effect of swing at two illumination angles cancels out, and the surface tilt or inclination can be uniquely determined by measuring the reflected light intensity from two angles of illumination. It will be understood that the invention may be practiced using more than two angles of illumination, to produce data which is theoretically redundant but which may be necessary in some practical applications.

It will be assumed that one of the curves 32 or 34 is rescaled such as to define a function R() such that $0 \leq R(t) \leq 1$, and $R(0) = 1$. A reasonable model of the image intensities sensed by the scanner 24 may be given as $$I_l = \alpha \cdot R(t-t_l) \cdot R(s) \qquad \text{(equ. 1a)}$$

$$I_h = \alpha \cdot R(t-t_h) \cdot R(s) \qquad \text{(equ. 1b)}$$

where t is the angle of tilt or inclination measured in this case from the horizontal, s is the angle of swing measured about the plane in which the scanner and light sources are mounted, $I_l$ is the sensed intensity with the low angle of illumination, $I_h$ is the sensed intensity with the high angle of illumination, R(s) is a function of swing, and $\alpha$ is a proportionality constant incorporating the albedo of the illuminated surface of the plate 20 and the characteristics of the light sources 26 and 28. The quantity $0 \leq R(t) \leq 1$ may be considered as a "reflectance" function. The light sources are adjusted such that when $s = 0$ and $t = t_l$, then numerical value of $I_l = 255$. This enables the reflectance function to be represented by an eight bit word.

In order to measure the height of a solder joint fillet such as 16b using the present shape by shading technique, a transformation is developed such that $$\Delta z / \Delta x = f(I_l, I_h)$$

where $\Delta z / \Delta x$ is the incremental change in solder fillet height along wall 16d of the fillet 16b as the wall 16d is optically scanned from a base 16f of the fillet 16b toward the lead 14, and f() is the desired transformation.

Equations 1a and 1b suggest the construction of a two dimensional array in the form of a look-up table indexed by $(I_l, I_h)$, containing tilt angles. All of the numerical values for the table may be obtained experimentally as described above. In cases where it is impossible or impractical to obtain all values for the table by actual measurement, some of the values may be obtained experimentally and the remaining values computed using an appropriate algorithm.

More specifically, the entries in the table may be obtained by incrementally varying the swing from 0° to 90° at each incremental value of tilt from 0° to 90°. Alternatively, the swing between 0° and 90° may be measured at only one value of tilt to obtain the function R(s) as illustrated in FIG. 5, and used to compute the table entries for the other values of tilt and swing using equations 1a and 1b. As yet another alternative, since the function R(s) represented by the swing curve 36 is so closely approximated by the tilt curve 32 as illustrated in FIG. 6, one of the tilt curves may be rescaled and used as the function of R(s) rather than experimentally measured values of swing. This observation makes it possible to obtain the entries for the look-up table using only measured values of tilt.

Where the array of entries stored in the look-up table must include more incremental values than it is practical to measure directly, gaps in the table may be filled in using an appropriate interpolation algorithm. A modified version of the medial axis transform algorithm described in a textbook entitled "Computer Vision", by D. Ballard et al, Prentice-Hall, Inc., 1982, pp. 252-253, is especially suitable for the purpose. The original medial axis transform algorithm provides a way to calculate the distance from each pixel to the nearest boundary of some arbitrary shape. Treating measured values in the array corresponding to equations 1a and 1b as "boundary" pixels, and modifying the original algorithm such that at every iteration each pixel copies the tilt value of that neighbor closest to a boundary pixel, the entire table will be filled with tilt values as the algorithm converges. Other suitable algorithms include bilinear interpolation and two dimensional splining.

Since the magnification of the system is known, the approximate width of a pixel in real space is also known. More specifically, $$\Delta z / \Delta x = \tan(t)$$

$$\Delta z = \Delta x \cdot \tan(t)$$

$$\Delta z(I_l, I_h) = \Delta x \cdot \tan(f(I_l, I_h))$$

where $\Delta x$ is the pixel spacing, or the spacing between incremental points at which the solder joint fillet is scanned in accordance with the invention.

By computing the tangent of each entry in the tilt table f(), and multiplying by $\Delta x$, a new look-up table $\Delta z()$, indexed by $(I_l, I_h)$ is produced. This is the array or lookup table used to actually practice the invention, and need be computed only once. Programs using $\Delta z$ information to detect solder joint defects can simply utilize a precomputed version of the $\Delta z()$ table stored in a hardware or software file. This approach enables rapid processing, since no redundant computing is performed.

Figure 7:
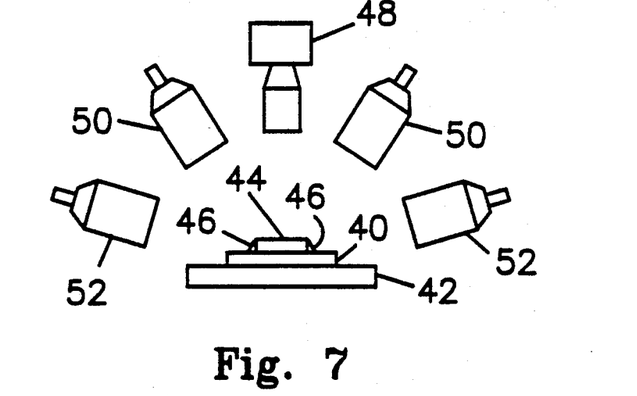
FIGS. 7 and 8 are simplified schematic diagrams illustrating alternative illumination and scanning embodiments of the invention.

FIG. 7 illustrates a first configuration of light sources and scanning means for practicing the present invention. A circuit board 40 is supported on a mount 42. An electrical component 44 such as an integrated circuit chip has leads which are connected to pads on the circuit board 40 by solder joints 46. Although not visible in the drawing, the circuit board 40 including the solder joints 46 is preferably coated with a material such as described above to reduce the albedo of the solder surface and make it substantially uniform. The mount 42 is preferably movable in the horizontal plane to sequentially locate the solder joints 46 at a position to be scanned.

A scanner 48, which may preferably be embodied by a CCD camera, is supported vertically above the mount 42 for scanning at least one solder joint 46, and storing a digitized or pixelized image representing the reflected light intensity or shading thereof in an internal analog memory. CCD cameras for performing this function are commercially available, and may typically store an eight bit pixelized image consisting of 480 × 512 pixels. The camera 48 may scan a single solder joint fillet, several fillets of a single solder joint, or several solder joints.

Although it is within the scope of the present invention to optically scan the solder joints directly, this is a very slow process. Preferably, the CCD camera takes an instantaneous picture of the solder joint in the form of the pixelized image, which is then scanned electronically to retrieve the numerical values corresponding to the individual pixels.

The arrangement illustrated in FIG. 7 further includes upper light sources 50 for illuminating the circuit board 40 from a first inclination angle, and lower light sources 52 for illuminating the circuit board 40 from a second, lower illumination angle. The light sources 50 and 52 preferably emit directional beams of light, such that the direction of illumination is constant within the camera's field of view, and may be embodied by optical fiber bundles. The axes of the camera 48 and light sources 50 and 52 are preferably located in a single vertical plane, although the invention is not so limited.

Two each of the light sources 50 and 52 are utilized in an application where it is desired to scan more than one solder fillet simultaneously with illumination from different directions respectively. Where only one solder fillet is to be scanned, or more than one solder fillet is to be scanned simultaneously with illumination from a single direction, only one each of the light sources 50 and 52 is required.

The apparatus is operated by turning on the light sources 50 with the light sources 52 turned off, and operating the scanner 48 to scan a portion of the circuit board 40 on which the selected solder joints 46 are located to produce a first pixelized image constituting the reflected light intensity values $I_h$. Then, the light sources 50 are turned off, the light sources 52 turned on, and the circuit board 40 is scanned to produce a second pixelized image constituting the reflected light intensity values $I_l$. Equivalent results may be obtained by reversing the order of turning the light sources 50 and 52 on and off.

Where the scanner 48 is capable of recording several individual, multicolor images simultaneously, for example three primary color images which may be combined to produce a full color image, the light sources 50 and 52 may produce light of two different colors or wavelengths, and the scanner 48 may produce separate images corresponding to the two colors respectively. This enables the invention to be practiced with one multicolor camera and two light sources, with the two images being obtained or scanned simultaneously.

Figure 8:
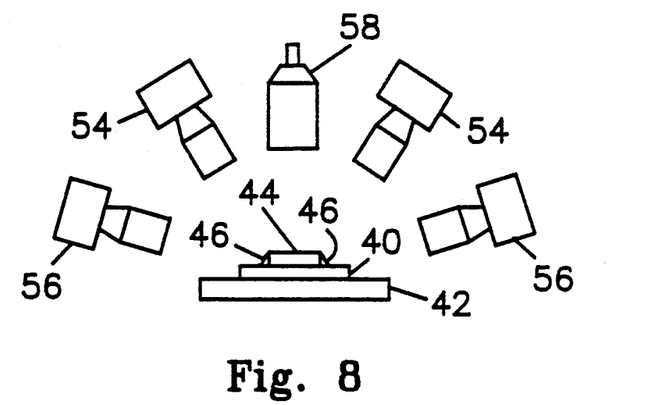

FIG. 8 illustrates a second configuration of the invention in which the relative positions of the scanning means and light sources are reversed. The results are equivalent, but the arrangement of FIG. 8 is advantageous in that both scans may be performed simultaneously. In FIG. 8, scanners 54 and 56 are mounted at the locations occupied by the light sources 50 and 52 respectively in FIG. 7. A single light source 58 is mounted in the position occupied by the scanner 48 in FIG. 7. In operation, the light source 58 is turned on, and the respective portions of the circuit board 40 scanned by the scanners 54 and 56 simultaneously. Although the arrangement of FIG. 8 operates twice as fast (for two illumination angles) as the arrangement of FIG. 7, the depth of focus of the cameras is restricted, and may not be sufficient for the system to operate properly.

Figure 9:
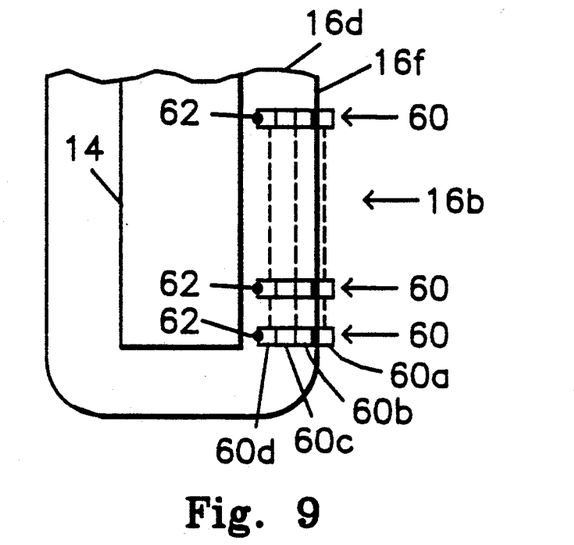
FIG. 9 is a simplified plan view of the solder joint of FIG. 1, illustrating a scanning arrangement utilized by the invention.
Figure 10:
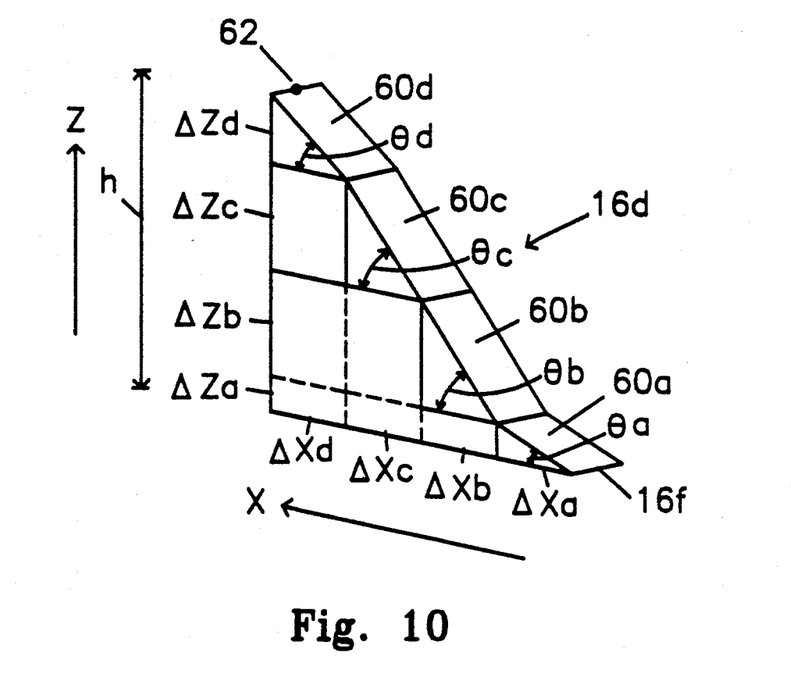
FIG. 10 is a perspective diagram illustrating how the height of a point on the solder joint of FIG. 9 is determined in accordance with the present invention.

Referring now to FIGS. 9 and 10, the scanning means produces a pixelized image of, for example, the wall 16d of the solder fillet 16b illustrated in FIG. 1 by scanning along lines 60 from the base 16f of the wall 16d to predetermined points 62 on the wall 16d spaced slightly outwardly from the lead 14. The points 62 represent the height profile of the wall 16d of the fillet 16b. The scan is schematically illustrated as being performed in four increments 60a, 60b, 60c and 60d, although in practical application the scan will include a much larger number of increments. The height values at the end points 62 of the scan lines 60 represent the incremental height values of the wall 16d of the solder fillet 16b at the predetermined points 62 respectively.

As viewed in FIG. 10, the pixels or increments 60a to 60d are oriented at tilt or inclination angles $\theta a$ to $\theta d$ respectively with respect to the horizontal, which correspond to the tilt angles t presented above. The angles $\theta a$ to $\theta d$ are obtained from the reflected light intensity values measured at the two illumination angles by accessing the array stored in the look-up table as described above. Horizontal scan increments $\Delta xa$ to $\Delta xd$ are equal, since the scan is performed at equal incremental points. Vertical height increments $\Delta za$ to $\Delta zd$ are equal to the constant scan increment value multiplied by the tangent of the inclination angle $\theta$, and are precomputed and stored in the array look-up table $\Delta z(I_l,I_h)$ as described above. Thus, each incremental height value is obtained by accessing the array with the sensed values of reflected light intensity $(I_l,I_h)$ at the two illumination angles. The height of the solder fillet wall 16d at the predetermined point 62 is obtained by summing the incremental height values $\Delta za$ to $\Delta zd$. The height profile of the wall 16d consists of the summed height values along the lines 60, and may be represented by a one-dimensional array.

Figure 11:
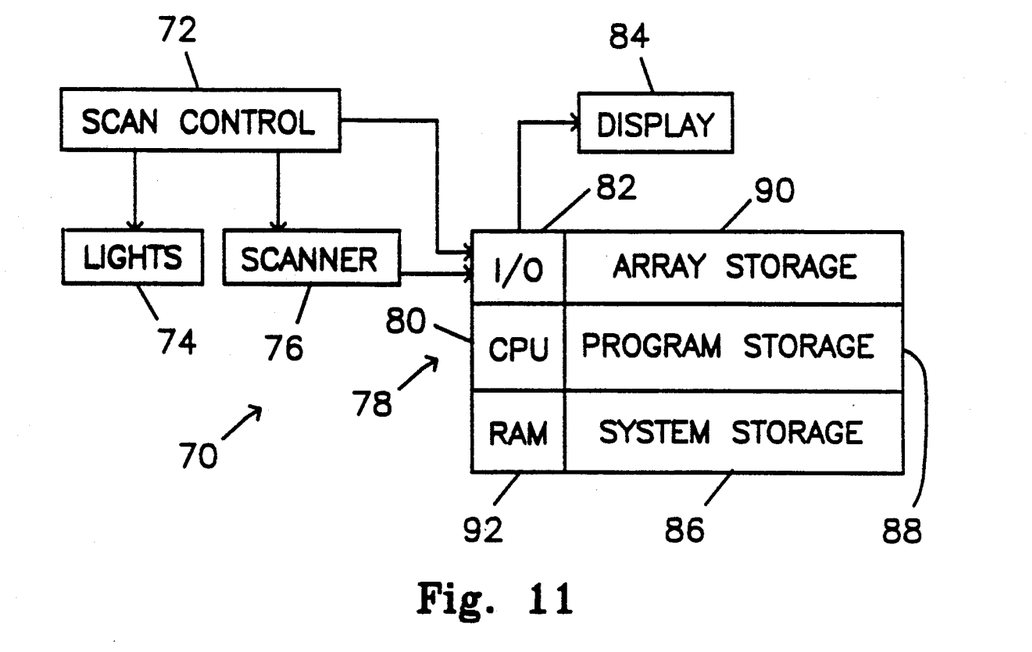
FIG. 11 is a block diagram of an apparatus for inspecting solder joints embodying the present invention.

An apparatus 70 for inspecting solder joints in accordance with the method of the present invention is illustrated in FIG. 11 and includes a scan control unit 72 which is constructed to control the lights 74 and a scanner 76 in accordance with the arrangement illustrated in FIG. 7 or 8. The reflected light intensity values produced by illumination and scanning of at least one solder joint are stored as pixelized images in the scanner 76.

The scanner 76 feeds the pixelized images into a computing unit which may be embodied by a conventional digital computer 78. The computer 78 has a central processing unit 80 for performing mathematical computations under program control, an input-output unit 82 for interfacing the computer 78 with the scanner 76 and an annunciator or display unit 84, an operating system storage unit 86, a program storage unit 88, an array storage unit 90, and a random access memory (RAM) unit 92 for dynamic storage of data and variables. The storage units 86 may include any combination of hardware and software, such as read-only memory (ROM), RAM, fixed or removable magnetic disks, magnetic tape, etc.

It will be understood that the computer 78 may be replaced by any combination of hardware and software which is capable of performing the required functions.

The unit 86 stores the operating system for the computer 78. The unit 88 stores the program utilized for operating on the pixelized images from the scanner 76 in accordance with the method of the invention. The unit 90 stores the $\Delta z(I_l,I_h)$ array in the form of a look-up table. More specifically, a numerical value of $\Delta z$ may be stored in each memory location which is accessed by x- and y-address values corresponding to the numerical values of $I_l$ and $I_h$ respectively.

Generally, the two pixelized images from the scanner 76 are stored in the RAM 92. The CPU 80, under control of the program stored in the storage unit 88, reads the values of $I_l$ and $I_h$ for each pixel location, and accesses the array stored in the unit 90 to obtain the corresponding value of $\Delta z$. The values of $\Delta z$ along each scan line are summed to obtain the height of the solder fillet wall at the respective point 62, and stored in the RAM 92 as a numerical value in a one-dimensional array which contains the height profile. The height profile is then operated upon in accordance with a predetermined inspection criterion stored as a program in the unit 88 to determine whether or not the corresponding solder fillet is defective. The results of the test may be displayed on the unit 84, or means (not shown) may be provided to automatically reject the circuit board containing the defective solder fillet.

Although the present invention is especially suited for automated inspection of solder joints, the principles thereof may be applied to measure the height of a predetermined point on a wall of any applicable object having a substantially uniform value of albedo.

Figure 12:
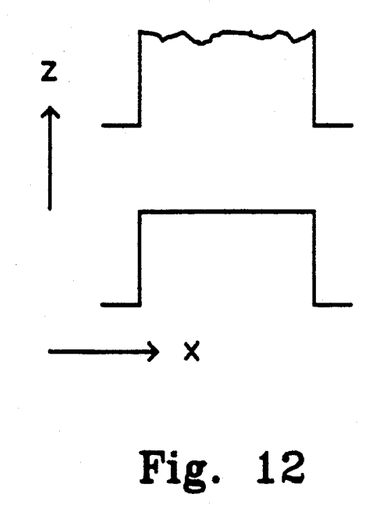
FIG. 12 is a graph illustrating electrical signals generated by the apparatus of FIG. 10 in response to scanning a good solder joint fillet.

FIG. 12 illustrates waveforms corresponding to a good solder fillet which may be generated on the display unit 84 by plotting the height profile stored in the one-dimensional array. The upper curve illustrates the unaltered data. The lower curve illustrates the data in smoothed form, resulting from operation on the data using a Schmitt trigger or other suitable signal processing means. Although the data in the upper curve has a value which varies along the wall of the fillet, it is high throughout its extent, indicating a continuously high fillet wall. The smoothed lower curve has a uniform high value.

Figure 13:
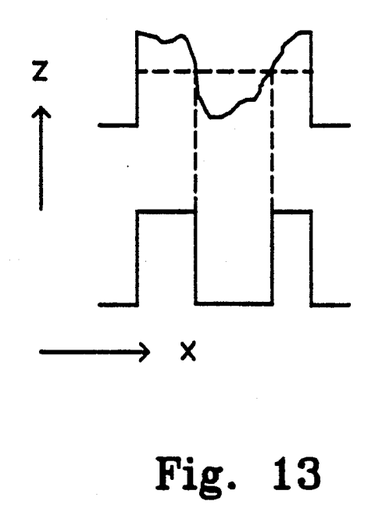
FIG. 13 is similar to FIG. 12, but illustrates signals generated in response to scanning a defective fillet.

FIG. 13 illustrates a defective solder joint having an area corresponding to 16e in FIG. 1, in which a portion of the lead 14 is exposed. Both the upper and lower curves have areas in which the fillet height decreases to a low value, corresponding to the defective area of the joint. A suitable criterion for evaluating the integrity of the solder joint in accordance with the height profiles may include rejecting the joint if there is any area with a height below a predetermined value, if there is more than one area with a height below a predetermined value, if there is a continuous area with a width longer than a predetermined value in which the height is below another predetermined value, etc. The particular criterion or algorithm for evaluating whether or not a particular solder joint is defective is not the subject of the present invention, and is specified by the user of the apparatus.

The present shape by shading technique utilizes the assumption that in the array $\Delta z(I_l, I_h)$, a single unique value of tilt or inclination t exists for each pair of reflected light intensities $(I_l, I_h)$. The following mathematical derivation proves that this is actually true.

The symmetric shape of R( ) indicates that its inverse is multivalued. Therefore, $R^{-1}(i) = \{t_1, t_2\}$, where i is a sensed intensity value and $t_1 \leq t_2$. The shape of R( ) dictates that $t_1 \neq t_2$ when $i \neq 255$, and that $t_2 - t_1$ changes with i. A new function W( ) can be defined having the following properties:

$$W(i) = t_2 - t_1,$$

where $R^{-1}(i) = \{t_1, t_2\}$ and $0 \leq i \leq 255$ setting $R^{-1}(0) = \{t_a, t_b\}$ then $W(0) = t_b - t_a$, $W(255) = 0$ and W( ) monotonically decreases with increasing i.

W(i) simply defines the "width" of R( ). The important observation is that W(i) = W(j), where j is another value of intensity, if and only if i = j. W( ) may be applied in solving equations 1a and 1b for tilt t:

$$I_l/[255 \cdot R(s)] = R(t - t_l) \quad \text{from equ. 1a}$$

$$R^{-1}[I_l/(255 \cdot R(s))] = \{t - t_l,\, t - t_l + w_l\} \quad \text{(equ. 2a)}$$

where $w_1 = W(R(t - t_l))$ $$I_h/[255\, R(s)] = R(t - t_h) \quad \text{from equ. 1b}$$

$$R^{-1}[I_h/(255 \cdot R(s))] = \{t - t_h,\, t - t_h + w_h\} \quad \text{(equ. 2b)}$$

where $w_h = W(R(t - t_h))$

In equations 2a and 2b, the identity $R^{-1}(i) = \{t_1, t_1 + W(i)\}$ has been used. Since the high and low light sources are at different orientations, $t_h \neq t_l$. For multiple tilts to exist for a given $I_l$ and $I_h$, the solutions to equations 2a and 2b must pair in one of the following ways:

Case 1: $t - t_l = t - t_h$
and $t - t_l + w_l = t - t_h + w_h$
Case 2: $t - t_l + w_l = t - t_h$
and $t - t_h + w_h = t - t_l$ But since $t_h \neq t_l$ in the first equation of Case 1 cannot be true, this leaves only Case 2. The first equation in case 2 implies $t_h = t_l - w_l$. Substituting this into the second equation of Case 2 yields:

$$t - t_l + w_l + w_h = t - t_l$$

or just $w_l = -w_h$ implying $w_l = w_h = 0$ which implies $$I_l = I_h \quad \text{(equ. 3)}$$

$w_l = 0$, implying that $t = t_l$. Substituting $t = t_l$ into equations 1a and 1b gives $$I_l = 255 \cdot R(t_l - t_l) \cdot R(s) = 255 \cdot R(s)$$

$$I_h = 255 \cdot R(t_l - t_h) \cdot R(s)$$

But $t_h \neq t_l$ implies $I_l \neq I_h$ above. This contradicts equation 3, and therefore Case 2 is not a viable option either. The uniqueness proof is thus complete, verifying that the $\Delta z(I_l, I_h)$ array look-up table technique embodying the present invention is valid.

The broad scope of the invention includes the determination of solder surface tilt as a predetermined function of reflected light intensity using means other than a two dimensional look-up table. The tilt may be computed in real time by solving an equation or set of equations either directly or by iteration which approximates the relationship between reflected light intensity and tilt using the sensed values of reflected light intensity as input variables. A further alternative method of practicing the invention includes computing the ratio of the two sensed reflected light intensities at each point, and using the ratio as an input to a one-dimensional look-up table or for real-time computation using an equation.

More specifically, since the reflectance model described in equations 1a and 1b above is variable separable, simply dividing one equation by the other would seem to greatly simplify the entire approach outlined thus far. Dividing equation 1a by equation 1b gives $$I_l(t)/I_h(t) = [\alpha \cdot R(t - t_l) \cdot R(s)] / [\alpha \cdot R(t - t_h) \cdot R(s)]$$

$$= R(t - t_l)/R(t - t_h)$$

The coefficient $\alpha$ and the factor introduced by the surface normal's swing, R(s), have both canceled, leaving a function of two known parameters ($t_l$ and $t_h$) and the desired unknown, t. To make this more clear, define a new function, Q(t), to be the quotient $I_l(t)/I_h(t)$ over those values of t for which $I_h(t)$ is not zero. Let $$Q(t) = I_l(t)/I_h(t) = R(t-t_l)/R(t-t_h), \forall t \text{ such that } R(t-t_h) \neq 0 \quad \text{(equ. 4)}$$

Since the functions $R(t-t_l)$ and $R(t-t_h)$ are known, the last equation above suggests that Q( ) could easily be constructed. However, the goal is to unambiguously recover the surface tilt, t. The desired function is $Q^{-1}($ ), and it should have the following property:

$$Q^{-1}[Q(t)] = Q^{-1}[I_l(t)/I_h(t)] = t$$

More simply put, for each unique value of t, there can only be a single corresponding value of $I_l(t)/I_h(t)$. If two different values of t give rise to the same ratio $I_l(t)/I_h(t)$, then $Q^{-1}($ ) will be multivalued, creating ambiguity.

Figure 14:
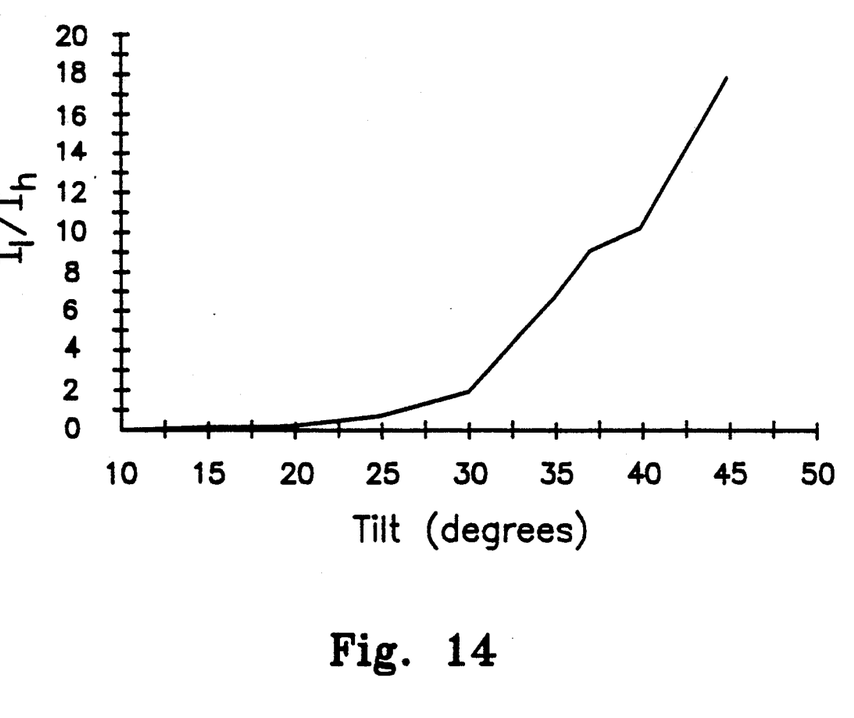
FIG. 14 is a graph illustrating an alternative embodiment of the invention.

FIG. 14 shows $I_l(t)/I_h(t)$ for tilts from 15° to 45°. The surprising result is that the quotient is a function which monotonically increases with tilt. If Q(11) is taken to be a continuous approximation of the curve shown in FIG. 14, then $Q^{-1}(11)$ is guaranteed to be a one to one mapping from $I_l(t)/I_h(t)$ to t.

Using this information for the recovery of unambiguous tilt values includes the following steps.

1. Create one dimensional $I_l(t)$ and $I_h(t)$ tables as described previously.
2. Create a one dimensional table Q(t) by dividing $I_l(t)$ by $I_h(t)$ (or vice-versa) for all those values of t where the denominator is not zero.
3. Construct the $Q^{-1}(11)$ table with these substeps:
   a. Let r be the smallest value greater than zero in Q().
   b. Set $Q^{-1}([Q(t)/r]) = t$, where [Q(t)/r] truncates the fractional part of Q(t)/r. It will be noted that $I_l(t)/I_h(t)$ can be very small (much less than 1), but an integer is required to address a look-up table. Consequently, [Q(t)/r] is required to rescale and "integerize" Q(t).
4. Compute a Δz() table as before, such that $\Delta z(i) = \Delta x \cdot \tan(Q^{-1}(i))$.
5. As in the two dimensional look-up table case, digitize one image under the high light source, and one image under the low light source.
6. At each pixel location calculate $[[I_l(t)/I_h(t)]/r]$ and use it to index Δx( ).
7. Sum the values of Δz( ) as in the two dimensional look-up table case to recover the surface height values.

The use of a single one dimensional look-up table seems more preferable than using a two dimensional table since less memory is used, and one dimensional array indexing is faster than two dimensional indexing. However, there are two serious implementation problems which, in some cases, can render the one dimensional look-up table approach impractical. In particular, the division of $I_l(t)$ by $I_h(t)$ and subsequent multiplication by 1/r may actually take more time than is gained by using a one dimensional look-up table. The second difficulty lies in the strong dependence of Q( ) and $Q^{-1}($ ) exact shape of $I_l(t)$ and $I_h(t)$. In the two dimensional look-up table case, weak constraints on R( ) were sufficient to guarantee the recovery of unique tilt values. In the one dimensional lookup table case, no such guarantee has been discovered, and the uniqueness properties must be tested experimentally.

Irrespective of whether one or two dimensional lookup tables are used, an important implementation detail is the positioning of the light sources. FIG. 3 indicates that $I_h(t)$ is zero for all t > 55°, and that $I_l(t)$ is at or near zero for all t < 10°. This indicates that a system using two lights positioned as in FIG. 2 cannot accurately recover tilts (if swing is nonzero) when the system tilt is less than 10° or greater than 55°. This is not a deficiency of the technique on the whole. In fact, the lighting of FIG. 2 has been shown to be adequate for solder joint inspection as discussed above. In general, if an application requires accurate recovery of a known range of tilt values, the lights are simply repositioned so that both $I_l(t)$ and $I_h(t)$ are nonzero in the required tilt range.

If the desired range of tilt values is so large (for instance 0° to 90°) that there are always some tilts which produce zero values for $I_l(t)$ or $I_h(t)$, additional light sources can be added. Suppose the light sources are numbered from one to n, where light number one is the highest light source, light source number 2 is the next highest, etc. Look-up tables are constructed for every pair of adjacent light sources just as described in the two light source case. To reconstruct surface heights, one image is taken under each of the n light sources; this yields n measurements $I_1, I_2, \ldots I_n$ for each pixel. For any pair of consecutive measurements, $I_k$ and $I_{k+1}$, in which $I_k$ and $I_{k+1} \neq 0$, the corresponding look-up table is indexed, $\Delta z_{k,k+1}(I_k, I_{k+1})$, to produce the local change in surface height. Here, $\Delta z_{k,k+1}($ ) is the look table corresponding to lights k and k+1. Summing Δz values along image rows is performed as described above. Depending on the application, a one dimensional look-up table indexed by a scaled, integerized version of $I_k/I_{k+1}$ could be used instead of a two dimensional look-up table.

While several illustrative embodiments of the invention have been shown and described, numerous variations and alternate embodiments will occur to those skilled in the art, without departing from the spirit and scope of the invention. Accordingly, it is intended that the present invention not be limited solely to the specifically described illustrative embodiments. Various modifications are contemplated and can be made without departing from the spirit and scope of the invention as defined by the appended claims.

I claim:

1. A method for determining the height of a solder fillet at a predetermined point on a wall thereof, comprising the steps of:
    (a) storing an array of predetermined incremental solder surface height change values, each being a function of first and second predetermined reflected light intensity values resulting from illumination of a solder surface from first and second angles at predetermined incremental values of solder surface tilt and swing respectively;
    (b) optically scanning the solder fillet from the base of the wall to said predetermined point while illuminating the fillet from the first angle, and sensing first reflected light intensity values at incremental points of said scan respectively;
    (c) optically scanning the fillet from a base of the wall to said predetermined point while illuminating the fillet from the second angle, and sensing second reflected light intensity values at the incremental points of said scan respectively;
    (d) accessing the array to obtain incremental height change values corresponding to the sensed first and second reflected light intensity values at the incremental points of said scan respectively; and
(e) summing the accessed height change values to obtain the height of the solder fillet at said predetermined point.

2. A method as in claim 1, in which:
steps (b) and (c) are performed sequentially and comprise, in combination, providing a single optical scanning means and first and second light source means oriented at the first and second angles respectively relative to the scanning means;
step (b) includes illuminating the fillet with only the first light source means; and
step (c) includes illuminating the fillet with only the second light source means.

3. A method as in claim 1, in which steps (b) and (c) are performed simultaneously and comprise, in combination, providing a single light source means and first and second optical scanning means oriented at the first and second angles respectively relative to the light source means.

4. A method as in claim 1, in which step (a) comprises the substeps of:
(f) illuminating the solder surface from the first angle at the predetermined incremental values of solder surface tilt and swing, and measuring the reflected light intensity of the solder surface to obtain the first predetermined reflected light intensity values respectively;
(g) illuminating the solder surface from the second angle at the predetermined incremental values of solder surface tilt and swing, and measuring the reflected light intensity of the solder surface to obtain the second predetermined reflected light intensity values respectively; and
(h) computing the height change values as a function of the predetermined incremental values of solder surface tilt and a spacing between the incremental points of said scan respectively.

5. A method as in claim 4, in which step (h) comprises multiplying the spacing between the incremental points of said scan by tangents of the angles of tilt of the solder surface at the predetermined values of solder surface tilt respectively.

6. A method as in claim 1, in which step (a) comprises the substep of:
(f) illuminating the solder surface from the first angle and a predetermined value of solder surface swing at the predetermined incremental values of solder surface tilt, and measuring the reflected light intensity of the solder surface to obtain first reflected light intensity values respectively;
(g) illuminating the solder surface from the second angle and said predetermined value of solder surface swing at the predetermined incremental values of solder surface tilt, and measuring the reflected light intensity of the solder surface to obtain second reflected light intensity values respectively;
(h) computing first and second reflected light intensity values as a predetermined function of said first and second measured reflected light intensity values and solder surface swing, at the predetermined incremental values of solder surface tilt and the incremental values of solder surface swing other said predetermined value of solder surface swing; the first and second predetermined reflected light intensity values including said measured and computed first and second reflected light intensity values in combination; and
(i) computing the height change values as a function of the predetermined incremental values of solder surface tilt and a spacing between the incremental points of said scan respectively.

7. A method as in claim 6, in which step (i) comprises multiplying a spacing between the incremental points of said scan by tangents of the angles of tilt of the solder surface at the predetermined values of solder surface tilt respectively.

8. A method as in claim 1, further comprising the step, performed before step (a), of:
(f) coating the solder surface with a material selected such that the coated solder surface has substantially uniform albedo;
the method further comprising the step, performed before steps (b) and (c), of:
(g) coating the wall of the fillet with said material.

9. A method as in claim 8, in which said material has a lower albedo than the solder surface and the wall of the fillet.

10. A method for inspecting a wall of a solder fillet, comprising the steps of:
(a) storing an array of predetermined incremental solder surface height change values, each being a function of first and second predetermined reflected light intensity values resulting from illumination of a solder surface from first and second angles at predetermined incremental values of solder surface tilt and swing respectively;
(b) optically scanning the solder fillet along a plurality of lines extending from a base of the wall to predetermined points on the wall while illuminating the fillet from the first angle, and sensing first reflected light intensity values at incremental points of said scan respectively;
(c) optically scanning the solder fillet along said plurality of lines extending from the base of the wall to said predetermined points on the wall while illuminating the fillet from the second angle, and sensing second reflected light intensity values at incremental points of said scan respectively;
(d) accessing the array to obtain incremental height change values corresponding to the sensed first and second reflected light intensity values at the incremental points of said scan respectively;
(e) summing the accessed height change values along said plurality of lines to obtain the heights of the solder fillet at said predetermined points respectively; and
(f) comparing said heights with a predetermined inspection criterion.

11. A method as in claim 10, in which:
steps (b) and (c) are performed sequentially and comprise, in combination, providing a single optical scanning means and first and second light source means oriented at the first and second angles respectively relative to the scanning means;
step (b) includes illuminating the fillet with only the first light source means; and
step (c) includes illuminating the fillet with only the second light source means.

12. A method as in claim 10, in which steps (b) and (c) are performed simultaneously and comprise, in combination, providing a single light source means and first and second optical scanning means oriented at the first and second angles respectively relative to the light source means.

13. A method as in claim 10, further comprising the step, performed before step (a), of:
    (g) coating the solder surface with a material selected such that the coated solder surface has substantially uniform albedo;
    the method further comprising the step, performed before steps (b) and (c), of:
    (h) coating the wall of the fillet with said material.

14. A method as in claim 13, in which said material has a lower albedo than the solder surface and the wall of the fillet.

15. A method for determining the height of a predetermined point on a wall of an object having a substantially uniform value of albedo, comprising the steps of:
    (a) storing an array of predetermined incremental surface height change values, each being a function of first and second predetermined reflected light intensity values resulting from illumination of a surface having said substantially uniform value of albedo from first and second angles at predetermined incremental values of surface tilt and swing respectively;
    (b) optically scanning the wall from a base thereof to said predetermined point while illuminating the wall from the first angle, and sensing first reflected light intensity values at incremental points of said scan respectively;
    (c) optically scanning the wall from a base thereof to said predetermined point while illuminating the fillet from the second angle, and sensing second reflected light intensity values at the incremental points of said scan respectively;
    (d) accessing the array to obtain incremental height change values corresponding to the sensed first and second reflected light intensity values at the incremental points of said scan respectively; and
    (e) summing the accessed height change values to obtain the height of the wall at said predetermined point.

16. A method as in claim 15, in which:
    steps (b) and (c) are performed sequentially and comprise, in combination, providing a single optical scanning means and first and second light source means oriented at the first and second angles respectively relative to the scanning means;
    step (b) includes illuminating the wall with only the first light source means; and
    step (c) includes illuminating the wall with only the second light source means.

17. A method as in claim 15, in which steps (b) and (c) are performed simultaneously and comprise, in combination, providing a single light source means and first and second optical scanning means oriented at the first and second angles respectively relative to the light source means.

18. A method for determining the height of a predetermined point on a wall of an object having a substantially uniform value of albedo, comprising the steps of:
    (a) storing an array of predetermined incremental surface height change values, each being a function of predetermined reflected light intensity values resulting from illumination of a surface having said substantially uniform value of albedo from a predetermined angle at predetermined incremental values of surface tilt and swing respectively;
    (b) optically scanning the wall from a base thereof to said predetermined point while illuminating the wall from said predetermined angle, and sensing reflected light intensity values at incremental points of said scan respectively;
    (c) accessing the array to obtain incremental height change values corresponding to the sensed reflected light intensity values at the incremental points of said scan respectively; and
    (d) summing the accessed height change values to obtain the height of the wall at said predetermined point.

19. An apparatus for determining the height of a solder fillet at a predetermined point on a wall thereof, comprising:
    storage means for storing an array of predetermined incremental solder surface height change values, each being a function of first and second predetermined reflected light intensity values resulting from illumination of a solder surface from first and second angles at predetermined incremental values of solder surface tilt and swing respectively;
    scanning means for optically scanning the solder fillet from a base of the wall to said predetermined point while illuminating the fillet from the first angle, and sensing first reflected light intensity values at incremental points of said scan respectively; and optically scanning the fillet from the base of the wall to said predetermined point while illuminating the fillet from the second angle, and sensing second reflected light intensity values at the incremental points of said scan respectively;
    computing means for accessing the array stored in the storage means to obtain incremental height change values corresponding to the sensed first and second reflected light intensity values at the incremental points of said scan respectively; and summing the accessed height change values to obtain the height of the solder fillet at said predetermined point.

20. An apparatus as in claim 19, in which:
    the scanning means comprises a single optical scanner means and first and second light source means oriented at the first and second angles respectively relative to the scanning means; the scanning means illuminating the fillet with the first and second light source means sequentially.

21. An apparatus as in claim 19, in which the scanning means comprises a single light source means and first and second optical scanner means oriented at the first and second angles respectively relative to the light source means; the scanning means scanning the fillet with the first and second scanner means simultaneously.

22. An apparatus as in claim 19, further comprising a material for coating the wall of the fillet; the material being selected such that the coated wall has substantially uniform albedo; said solder surface utilized in obtaining the first and second predetermined reflected light intensity values for the array being coated with said material.

23. An apparatus as in claim 22, in which said material has a lower albedo than the solder surface and the wall of the fillet.

24. An apparatus for inspecting a wall of a solder fillet, comprising:
    storage means for storing an array of predetermined incremental solder surface height change values, each being a function of first and second predetermined reflected light intensity values resulting from illumination of a solder surface from first and second angles at predetermined incremental values of solder surface tilt and swing respectively;

scanning means for optically scanning the solder fillet along a plurality of lines extending from a base of the wall to predetermined points on the wall while illuminating the fillet from the first angle, and sensing first reflected light intensity values at incremental points of said scan respectively; and optically scanning the fillet along said plurality of lines extending from the base of the wall to said predetermined points while illuminating the fillet from the second angle, and sensing second reflected light intensity values at the incremental points of said scan respectively;

computing means for:
accessing the array stored in the storage means to obtain incremental height change values corresponding to the sensed first and second reflected light intensity values at the incremental points of said scan respectively;
summing the accessed height change values along said plurality of lines to obtain the height of the solder fillet at said predetermined points respectively; and
comparing said heights with a predetermined inspection criterion.

25. An apparatus as in claim 24, in which:
the scanning means comprises a single optical scanner means and first and second light source means oriented at the first and second angles respectively relative to the scanning means; the scanning means illuminating the fillet with the first and second light source means sequentially.

26. An apparatus as in claim 24, in which the scanning means comprises a single light source means and first and second optical scanner means oriented at the first and second angles respectively relative to the light source means; the scanning means scanning the fillet with the first and second scanner means simultaneously.

27. An apparatus as in claim 24, further comprising a material for coating the wall of the fillet; the material being selected such that the coated wall has substantially uniform albedo; said solder surface utilized in obtaining the first and second predetermined reflected light intensity values for the array being coated with said material.

28. An apparatus as in claim 27, in which said material has a lower albedo than the solder surface and the wall of the fillet.

29. A method for determining a height difference between two points on solder fillet, comprising the steps of:
(a) optically scanning the fillet in a first scan between said two points while illuminating the fillet form a first angle;
(b) sensing the reflected light intensity of the fillet at incremental points along said first scan;
(c) optically scanning the fillet in a second scan between said two points along the same path as the first scan while illuminating the fillet from a second angle which lies in the same plane as said first angle;
(d) sensing the reflected light intensity of the fillet at incremental points along said second scan; and
(e) determining said height difference between said two points by computing said height difference as a predetermined function of said sensed reflected light intensities during the two scans.

30. A method as in claim 29, in which step (e) comprises the substeps of:
(f) computing the ratio of the sensed reflected light intensities; and
(g) computing said height difference as a predetermined function of said ratio.

31. A method as in claim 29, in which said predetermined function comprises a one dimensional look-up table.

32. A method for determining the height of a solder fillet at a predetermined point on a wall thereof, comprising the steps of:
(a) storing an array of predetermined incremental solder surface height change values, each being a function of first and second predetermined reflected light intensity values resulting from illumination of a solder surface from first and second angles at predetermined incremental values of solder surface tilt and swing respectively;
(b) optically scanning the solder fillet from the base of the wall to said predetermined point while illuminating the fillet from the first angle, and sensing first reflected light intensity values at incremental points of said scan respectively;
(c) optically scanning the fillet from a base of the wall to said predetermined point while illuminating the fillet from the second angle, and sensing second reflected light intensity values at the incremental points of said scan respectively;
(d) accessing the array to obtain incremental height change values corresponding to the sensed first and second reflected light intensity values at the incremental points of said scan respectively; and
(e) summing the accessed height change values to obtain the height of the solder fillet at said predetermined point;
steps (b) and (c) being performed simultaneously and including, in combination, providing a single optical scanning means capable of performing individual scans in response to light of first and second wavelengths respectively; and first and second light source means which emit light at the first and second wavelengths and are oriented at the first and second angles respectively relative to the scanning means.

* * * * *